(12) United States Patent
Todokoro et al.

(10) Patent No.: US 7,742,794 B2
(45) Date of Patent: Jun. 22, 2010

(54) PROBE ADAPTED TO BE USED WITH PULSE OXIMETER

(75) Inventors: Noriaki Todokoro, Tokyo (JP); Keiichi Sugiura, Tokyo (JP); Toru Maeda, Tokyo (JP); Hideki Fujisaki, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 227 days.

(21) Appl. No.: 11/494,513

(22) Filed: Jul. 28, 2006

(65) Prior Publication Data

US 2007/0027376 A1    Feb. 1, 2007

(30) Foreign Application Priority Data

Jul. 29, 2005  (JP)  ............ P2005-220556
Nov. 11, 2005  (JP)  ............ P2005-327006

(51) Int. Cl.
*A61B 5/145*  (2006.01)
(52) U.S. Cl. ............... 600/344; 600/323
(58) Field of Classification Search ........... 600/323, 600/344
See application file for complete search history.

(56) References Cited

U.S. PATENT DOCUMENTS

| | | | |
|---|---|---|---|
| 4,685,464 A | 8/1987 | Goldberger et al. | |
| 5,776,059 A | 7/1998 | Kaestle et al. | |
| 5,810,724 A * | 9/1998 | Gronvall | 600/323 |
| 6,343,223 B1 * | 1/2002 | Chin et al. | 600/323 |
| 7,272,426 B2 | 9/2007 | Schmid | |
| 2002/0156354 A1 * | 10/2002 | Larson | 600/344 |
| 2004/0204635 A1 | 10/2004 | Scharf et al. | |

FOREIGN PATENT DOCUMENTS

JP          2547840 Y2    5/1997
WO    WO 2004/069046   *  8/2004

* cited by examiner

*Primary Examiner*—Eric F Winakur
*Assistant Examiner*—Etsub D Berhanu
(74) *Attorney, Agent, or Firm*—Sughrue Mion, PLLC

(57) ABSTRACT

A probe adapted to be used with a pulse oximeter is disclosed. A flexible first housing is adapted to be brought into contact with at least a nail of a finger or a toe of a subject. A flexible second housing is adapted to be brought into contact with at least a top of the finger or the toe. A flexible connecting part connects the first housing and the second housing, and is adapted to cover a tip end of the nail. A light emitting element is provided on one of the first housing and the second housing. A light receiving element is provided on the other one of the first housing and the second housing.

11 Claims, 7 Drawing Sheets

PROBE ADAPTED TO BE USED WITH PULSE OXIMETER

BACKGROUND OF THE INVENTION

The present invention relates to a probe adapted to be used with a pulse oximeter which enables measurement of oxygen saturation of arterial blood ($SpO_2$) while being attached to a finger of a hand or a toe of a foot of a subject.

For measurement of the oxygen saturation of arterial blood of a subject, there has hitherto been used a probe adapted to be used with a pulse oximeter. In the pulse oximeter, a light emitting element and a light receiving element, which pair up with each other, are disposed opposite each other with a piece of tissue of a living body interposed therebetween, and oxygen saturation of arterial blood is determined by measuring the intensity of the light having passed through the tissue of the living body.

A probe, which has hitherto been known as a probe for a pulse oximeter of this type, has housings to which, e.g., a light emitting element and a light receiving element are mounted so as to oppose each other, and the housings are opened and closed while being pivoted around a joint shaft in the manner of a clothespin (see U.S. Pat, No. 4,685,464). With a spring (a clip), the light emitting element and the light receiving element are impelled so as to come close to each other. This probe is used for fingers of a hand, and the housings are attached to the finger of the subject in a pinching manner. That is, the subject's finger is sandwiched between the housings.

However, the two mutually-opposing housings are actuated around the joint shaft to thus open, or close. Hence, when variations exist among individuals in terms of thickness or size, as in the case of a finger, difficulty is encountered in causing a single probe to conform to all subjects. The probe cannot be appropriately attached to a finger which is greater than a predetermined thickness, and encounters difficulties of being displaced from a measurement site or becoming readily detached from the same. Since the spring force used for opening and closing the housings is specified, pain is inflicted when the probe is continuously attached over a long period of time. For this reason, the probe is inconvenient for use in, e.g., screening inspection of SAS (Sleep Apnea Syndrome), which requires attachment of a probe overnight.

In contrast with the probe adapted to be used with a pulse oximeter of such a spring (clip) type, there is also proposed another probe (see U.S. Pat. No. 5,776,059). The probe comprises a first casing section having a light receiving element, and a second casing section having a light emitting element, the casing sections being connected so as to be V-shaped. An adhesive member is provided at least on an interior surface of the first casing section. A nail of a finger or a toe of the subject is sandwiched between the first and second casing sections, to thus measure oxygen saturation of arterial blood. In order to fix this probe to the measurement site of the subject, providing the adhesive member to the interior surface of the casing section is indispensable.

The thus-configured probe is configured such that the first and second casing sections are connected so as to possess some degree of resilience. However, in order to cause the probe to be appropriately fixed to all fingers or the like, which vary in thickness or size among individuals, providing the adhesive member is indispensable. When dust, or the like, adheres to the adhesive member and this probe is reused, the accuracy of measurement is adversely affected, and a problem of sanitary administration is also raised.

Moreover, a disposable probe of an adhesive sheet structure has also been proposed as a probe which differs from the above-described probes in terms of structure (see Japanese Utility Model No. 2547840). However, when screening inspection of SAS is performed at home, the subject must wear this probe by himself/herself. In such a case, no limitations are imposed on a location where the probe is to be attached. However, attaching the probe to an appropriate measurement site requires knowledge or a technique. Further, the subject encounters difficulty in attaching the probe by himself or herself.

As mentioned previously, a required technique is required when the probe for a pulse oximeter is appropriately attached to a measurement site, and difficulty is encountered in the subject wearing the probe. Further, when the subject has attached the probe by himself/herself, the quality of measurement is often dependent on the state of attachment. For this reason, in order to accurately measure oxygen saturation of arterial blood, operation performed by a specialized engineer or by nursing personnel is required. There may be a case where long-duration attachment of the probe results in an increase in a sense of discomfort created by the living tissue in the measurement site, so that the subject takes the probe off consciously or subconsciously the probe for reasons of aches. Attaching the probe over a long period of time results in an increase in the chance of occurrence of a pressure mark, caused by localized pressure of the measurement site, and occurrence of blisters. Hence, the point where the probe is to be attached needs to be changed frequently, which in turn results in an increase in the burden imposed on the operator who performs measurement.

SUMMARY OF THE INVENTION

It is therefore an object of the invention to provide a probe adapted to be used with a pulse oximeter which enables positioning of a light emitting element and a light receiving element to a suitable measurement site at all times in order to appropriately measure oxygen saturation of arterial blood; which enables appropriate tentative fixing of the probe to the measurement site without provision of an adhesive member; which enables the subject to readily attach the probe without fail; and which can be used appropriately for screening inspection of SAS, for example.

It is also an object of the invention to provide a probe adapted to be used with a pulse oximeter which has a simple structure and can be manufactured at low cost; which is compact and lightweight and lessens the burden imposed on a subject even when the subject wears the probe for a long period of time; and which can be effectively and economically utilized as a reusable probe.

In order to achieve the above objects, according to the present invention, there is provided a probe adapted to be used with a pulse oximeter, comprising:

a flexible first housing, adapted to be brought into contact with at least a nail of a finger or a toe of a subject;

a flexible second housing, adapted to be brought into contact with at least a top of the finger of the toe;

a flexible connecting part, connecting the first housing and the second housing, and adapted to cover a tip end of the nail;

a light emitting element, provided on one of the first housing and the second housing; and a light receiving element, provided on the other one of the first housing and the second housing.

With this configuration, a probe equipped with a light emitting element and a light receiving element can be appropriately positioned to a measurement site at all times with a view toward appropriately measuring oxygen saturation of arterial blood ($SpO_2$). Further, the probe has the function of enabling tentative, appropriate fixing to the measurement site on the subject without provision of an adhesive member, which enables the subject to readily, reliably attach the probe. The probe can also be used for screening inspection of SAS, for example. Particularly, the probe for a pulse oximeter of the present invention is simple in structure and can be manufactured at low cost; is compact and lightweight and lessens the burden imposed on the subject even when the subject wears the probe for a long period of time; and can be effectively and economically utilized as a reusable probe.

The probe may further comprise a cushion member, provided on the first housing and adapted to brought into contact with the finger or the toe, the cushion member formed with an opening which allows light emitted from the light emitting element to pass therethrough.

A part of the opening may be adapted to be opposed to a nail root of the finger or the toe.

The cushioning member may include a first part having a first softness, and a second part adapted to be opposed to a nail root of the finger or the toe and having a second softness softer than the first softness.

With the above configurations, there is enhanced a shock-absorbing effect on an area which inflicts pain on a finger or a toe during attachment of the probe, thereby enabling long-duration attachment of the probe. The probe can be thus used for screening inspection of SAS, for example.

The probe may further comprise a pair of light shielding covers, provided on the first housing and adapted to be opposed to side portions of the finger or the toe so as to entirely cover the nail of the finger or the toe.

With this configuration, external light is reliably blocked during attachment of the probe, to thus enable highly-accurate measurement of oxygen saturation of arterial blood at all times.

A recess adapted to accommodate the tip end of the nail may be formed on an inner face of the connecting part.

With this configuration, the probe can be appropriately, reliably attached even to a subject having long nails, and highly-accurate measurement of oxygen saturation of arterial blood can be carried out.

The first housing, the second housing and the connecting part may be monolithically formed with flexible material comprised of resin, so that the first housing and the second housing are adapted to be elastically brought into contact with a tip end portion of the finger or the toe with a pressure falls within a range from a pressure at which a venous pulsation of peripheral blood vessel is reduced (e.g., 10 mmHg) to a pressure at which an arterial pulsation is not reduced (e.g., 35 mmHg).

With this configuration, the tentative fixability can be enhanced.

The probe may further comprise a lead wire, electrically connecting the pulse oximeter with each of the light emitting element and the light receiving element.

The probe may further comprise a communicator, electrically connected with each of the light emitting element and the light receiving element, and operable to communicate signals with the pulse oximeter in a wireless manner.

BRIEF DESCRIPTION OF THE DRAWINGS

The above objects and advantages of the present invention will become more apparent by describing in detail preferred exemplary embodiments thereof with reference to the accompanying drawings, wherein.

DETAILED DESCRIPTION OF THE EMBODIMENTS

Figure 1:
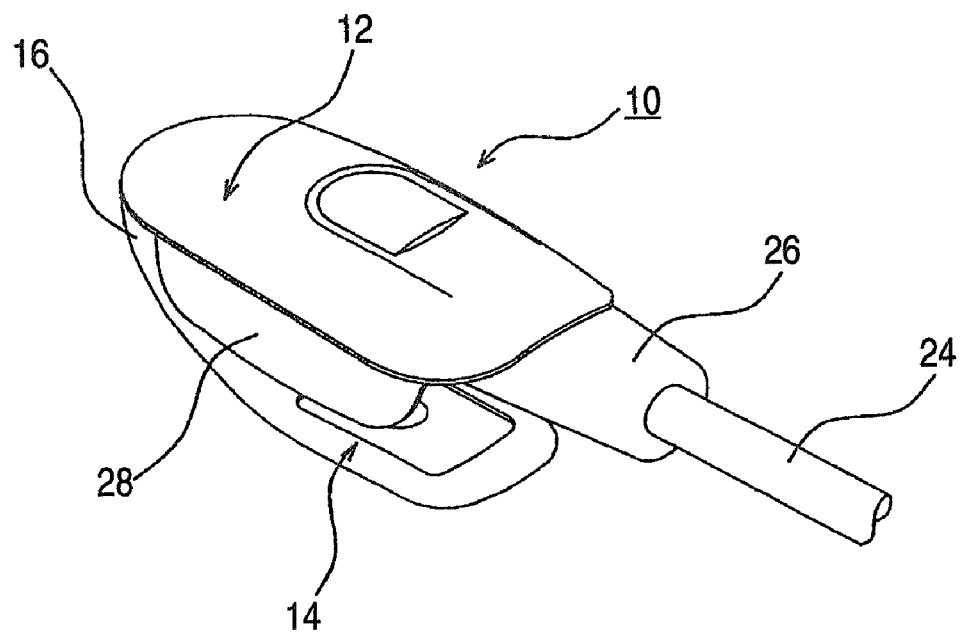
FIG. 1 is a rear perspective view of a probe according to one embodiment of the invention.
Figure 2:
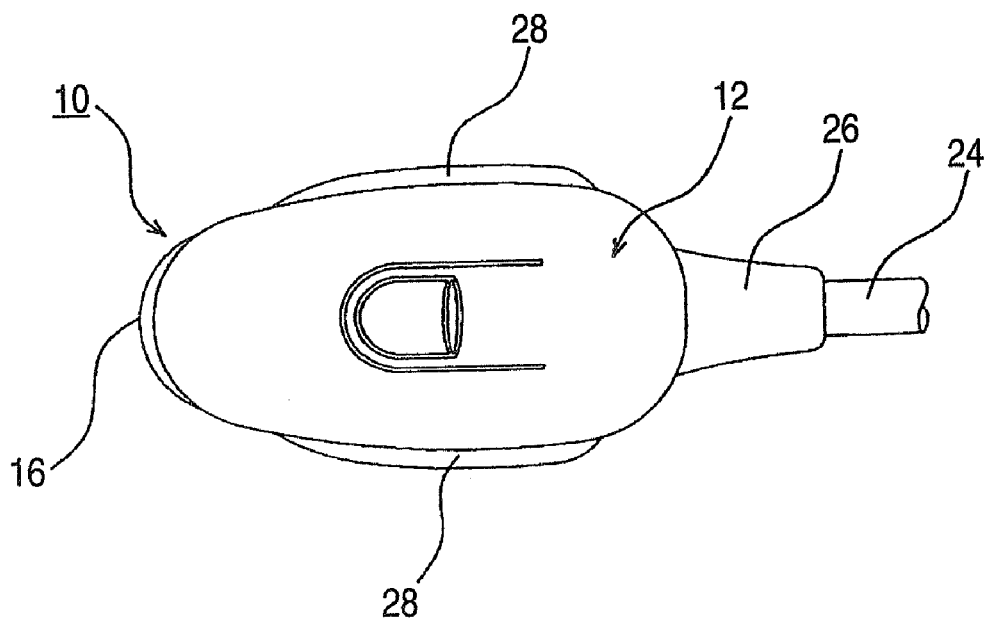
FIG. 2 is a top plan view of the probe.

Embodiments of a probe for a pulse oximeter according to the present invention will now be described below in detail with reference to the accompanying drawings.

As shown in FIGS. 1 through 6, a probe 10 adapted to be used with a pulse oximeter (hereinafter simply called as "probe") according to one embodiment of the present embodiment comprises a first housing 12 and a second housing 14 in which a light emitting element and a light receiving element are mounted so as to oppose each other. The first housing 12 is configured so as to fit and contact a nail of finger, and the second housing 14 is curved, while remaining continuous with the first housing 12, at a curved section 16 so as to cover the tip end of the nail and fits and contacts the top of the finger (see especially FIG. 3).

The probe 10 can be formed monolithically from a flexible resin material such that the pressure at which the first housing 12 contacts the tip end of the finger and the pressure at which the second housing 14 contacts the pulp of the finger have flexural elasticity of a range from a pressure (10 mmHg) at which a venous pulsation of a peripheral blood vessel is reduced to a pressure (30 to 35 mmHg) at which an arterial pulsation is not reduced. The curved section 16 may be formed from another flexible material having an elasticity, and the first housing 12 and the second housing 14 may be connected thereby, to thus realize a configuration analogous to the probe 10 of the embodiment.

Figure 7:
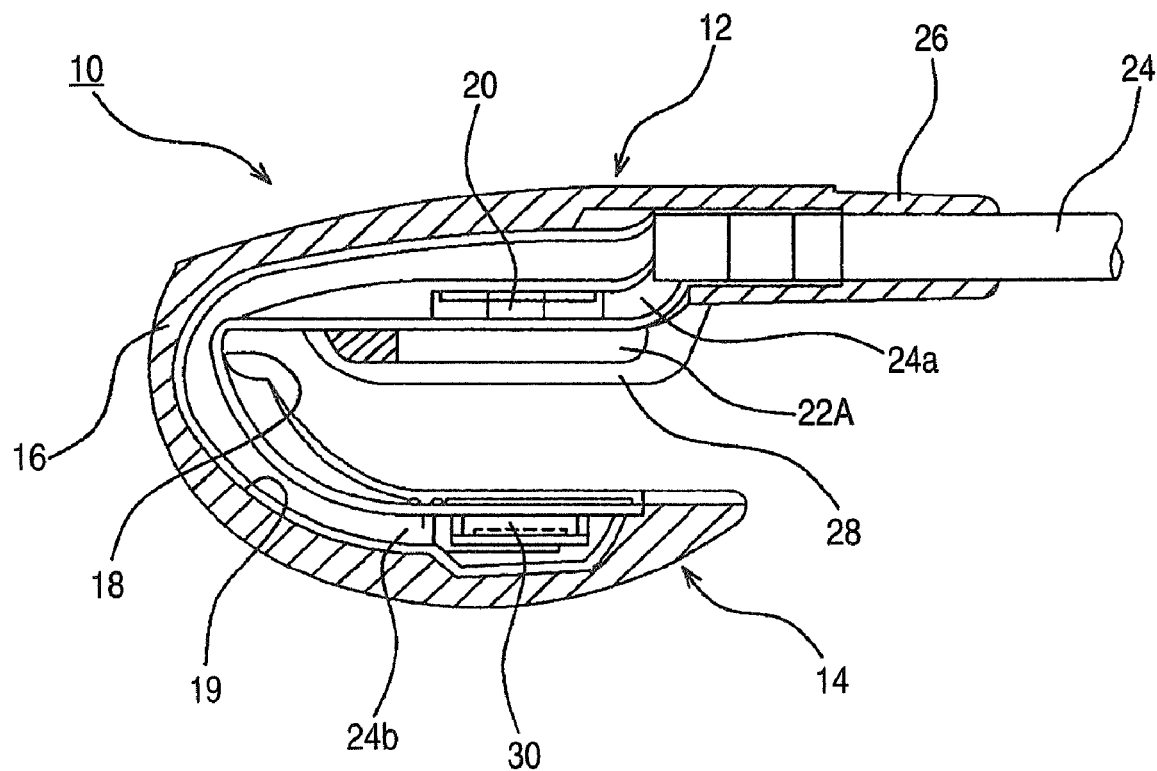
FIG. 7 is a sectional side view of the probe.
Figure 8A:
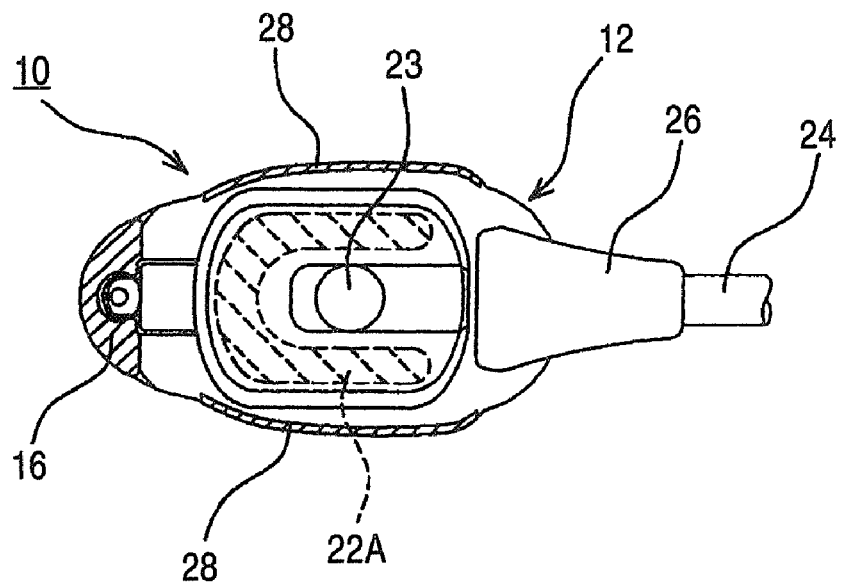
FIG. 8A is a bottom plan view of a first housing of the probe.
Figure 8B:
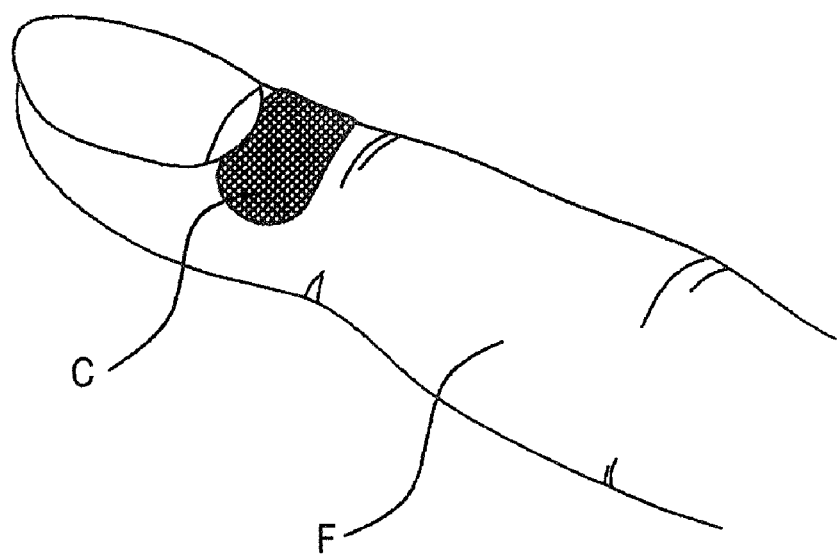
FIG. 8B is a perspective view of a finger of a subject, to which the probe is attached.

As shown in FIG. 7, a light emitting element 20 is housed in the first housing 12 of the probe 10. As shown in FIG. 8A, a U-shaped cushion member 22A is provided so as to prevent the first housing 12 from contacting the center C of the nail root of the fingertip F (see FIG. 8B). A light emitting window 23 for the light emitting element 20 is provided in the center of the U-shaped cushion member 22A. The center C at the nail root of the finger tip section F is known as the area where the skin is thin and an ache is likely to arise upon application of a pressure. Accordingly, at the time of attachment of the probe 10, the shock-absorbing effect for the area of the finger where pain is inflicted is enhanced, and long-duration attachment of the probe is enabled. The probe can be thus used for screening inspection of SAS, for example.

Figure 9A:
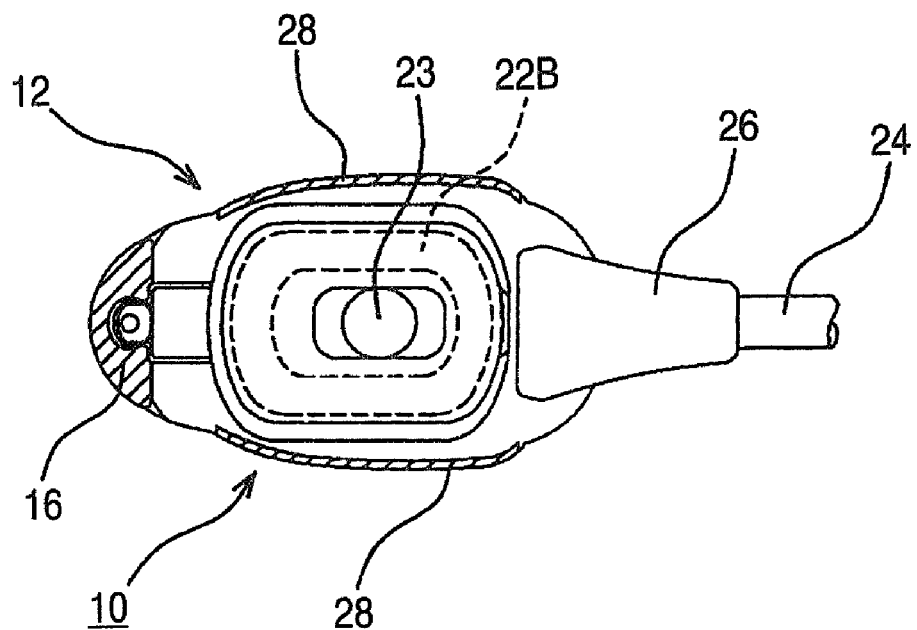
FIG. 9A is a bottom plan view of a modified example of the first housing of FIG. 7.
Figure 9B:
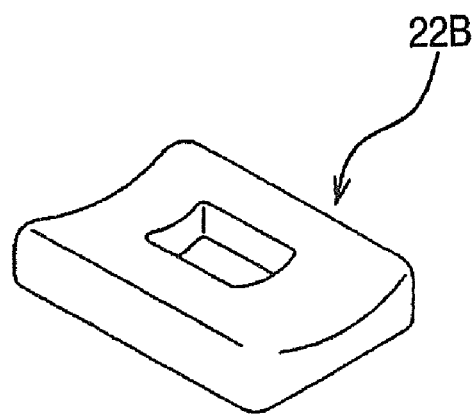
FIG. 9B is a perspective view of a cushion member in the first housing of FIG. 9A.

As shown in FIGS. 9A and 9B, the cushion member 22A may be replaced with an annular cushion member 22B in order to make the distribution of the pressure, which the cushion member 22B exerts on the center C of the nail root of the finger tip F, essentially equal to the pressure of the entire probe or weaker than the pressure distribution of the remaining portion of the probe even when the cushion member 22B contacts the center C of the nail root of the fingertip F. In this case, a hole section formed in the center of the cushion member 22B serves as the light emitting window 23 for the light emitting element 20.

In the cushion member 22B that is configured as above, a part of the cushion member contacting the center C of the nail root can lessen the pressure exerted on the center section C of the nail root by: (1) using a material which is softer than other part contacting both longitudinal sides of the fingertip section F; (2) forming the cushion member into a curved shape conforming to the shape of the finger; or (3) combining (1) with (2). The softer part can be embodied by sealing a sponge, air, liquid, or a gelling agent with a sheet material having a casing structure in order to enhance all elastic members or durability. In other words, inserting a raw material or substance which is softer than the other part into the sheet material. When the subject wears the probe 10 using the above cushion member 22B, the first housing 12 follows the shape of the finger, an ideal distribution of pressure without involvement of local pressure can be attained.

Accordingly, the probe 10 of the present invention enhances a shock-absorbing effect on an area which inflicts pain on a finger during attachment of the probe, thereby enabling long-duration attachment of the probe. The probe can be thus used for screening inspection of SAS, for example.

The shape of the cushion member may be changed such as a rectangular shape, a square shape, or a circular shape, so long as a hole section having such a size not covering the window 23 is provided.

A wire guiding section 26 to which a lead wire 24 connected to a probe connector (not shown) is inserted is formed in the rear end of the first housing 12. Moreover, light shielding covers 28, which are used for shielding external light are provided on both longitudinal sides of the first housing 12 and extended so as to completely cover the surface of the nail of finger. With such a configuration, highly-accurate measurement of oxygen saturation of arterial blood can be reliably performed without interference of the external light.

Figure 3:
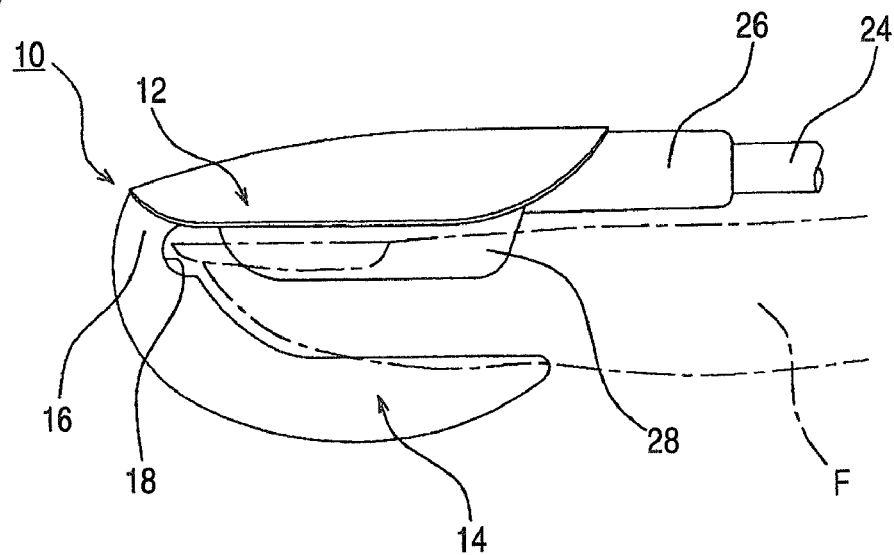
FIG. 3 is a schematic side view of the probe.
Figure 4:
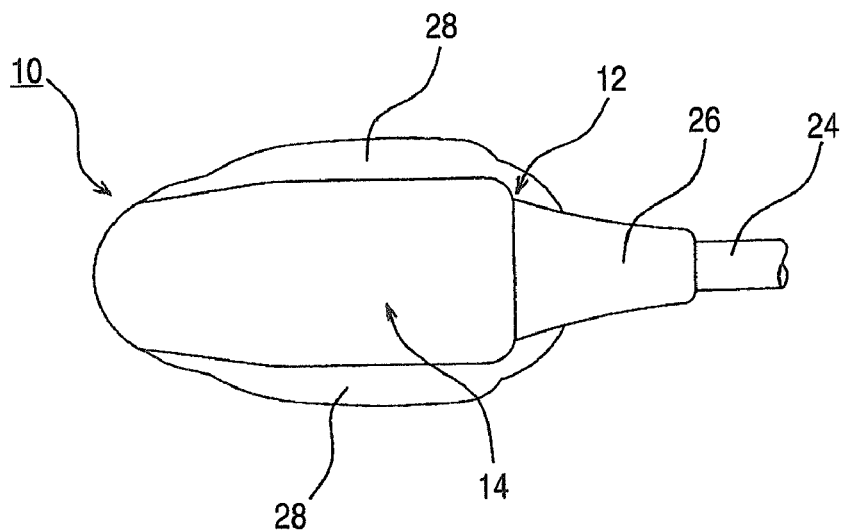
FIG. 4 is a bottom plan view of the probe.
Figure 5:
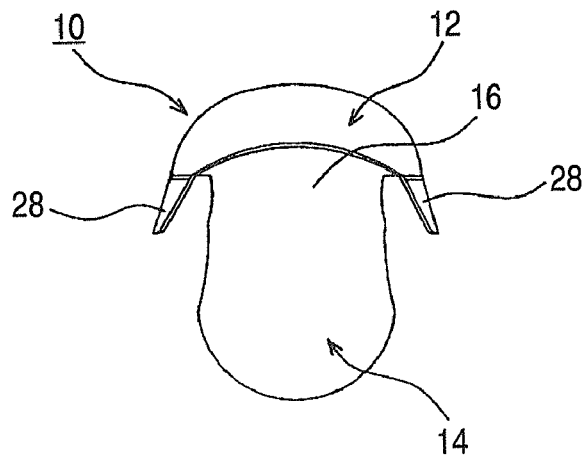
FIG. 5 is a front view of the probe.
Figure 6:
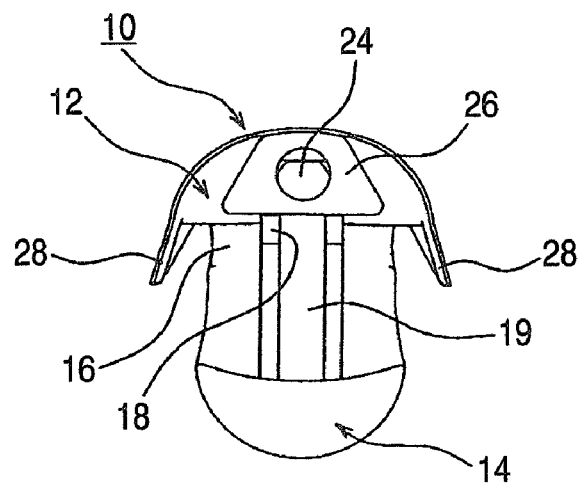
FIG. 6 is a rear view of the probe.

A recessed section 18, which can accommodate the tip end of the nail extended beyond the fingertip section F, is provided on the interior surface of the curved section 16 to which are connected the first housing 12 and the second housing 14 (see FIGS. 3 and 7). With this configuration, even a subject having long nails can safely, appropriately, and reliably wear the probe 10.

Figure 10:
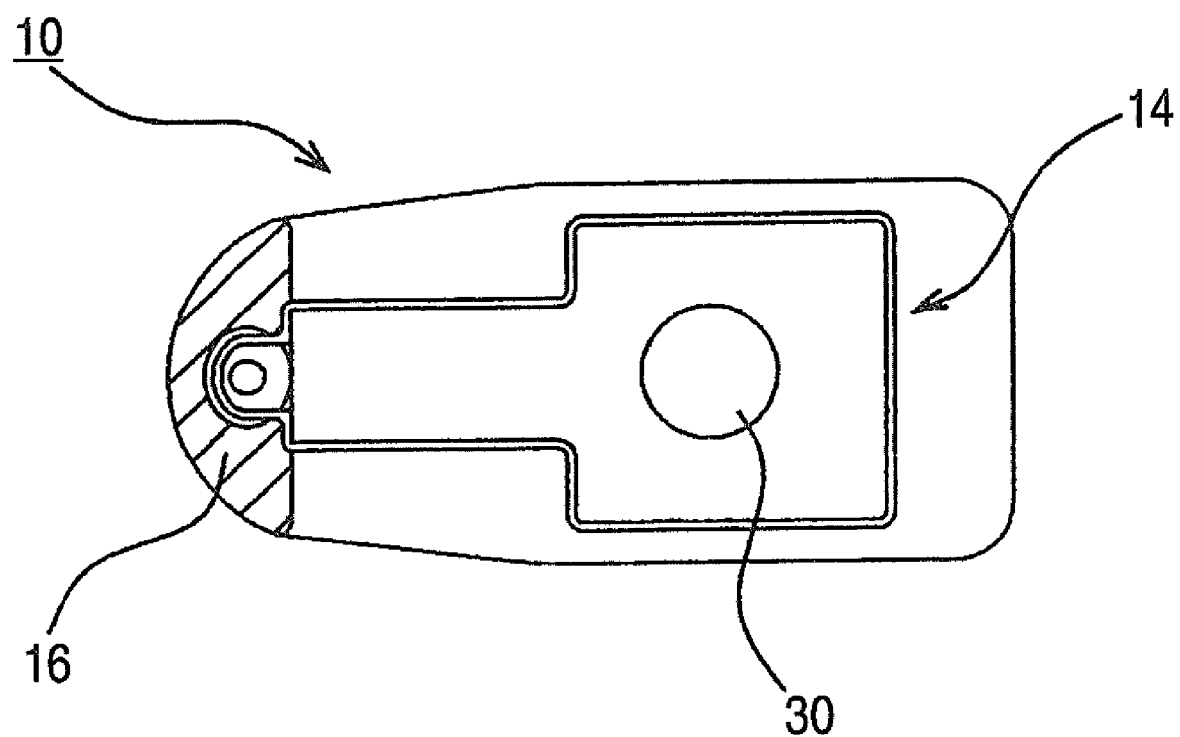
FIG. 10 is a top plan view of a second housing of the probe.

As shown in FIGS. 7 and 10, the light receiving element 30 is housed and arranged in the center on the interior surface of the second housing 14, and is brought into intimate contact with the pulp of the finger. With this configuration, the light receiving element 30 can be appropriately placed opposite the light emitting element 20, to thus enable highly-accurate measurement of oxygen saturation of arterial blood. In this case, a lead wire 24b of the light receiving element 30 is provided on the interior surface of the first housing 12 by way of a groove 19 which is formed from the interior surface of the second housing 14 to the interior surface of the curved section 16. The lead wire 24b is provided in conjunction with the lead wire 24a of the light emitting element 20, and led to the outside from the probe 10 as the external lead wire 24 to be connected to the probe connector (see FIGS. 6 and 7).

In this embodiment, the entire surface of the light emitting element 20 which is provided on the interior surface of the first housing 12, the entire surface of the cushion section 22, and the entire surface of the light receiving element 30 provided on the interior surface of the second housing 14 are covered with a protective cover (not shown), as appropriate. Reuse of the probe 10 is made more convenient.

Figure 11A:
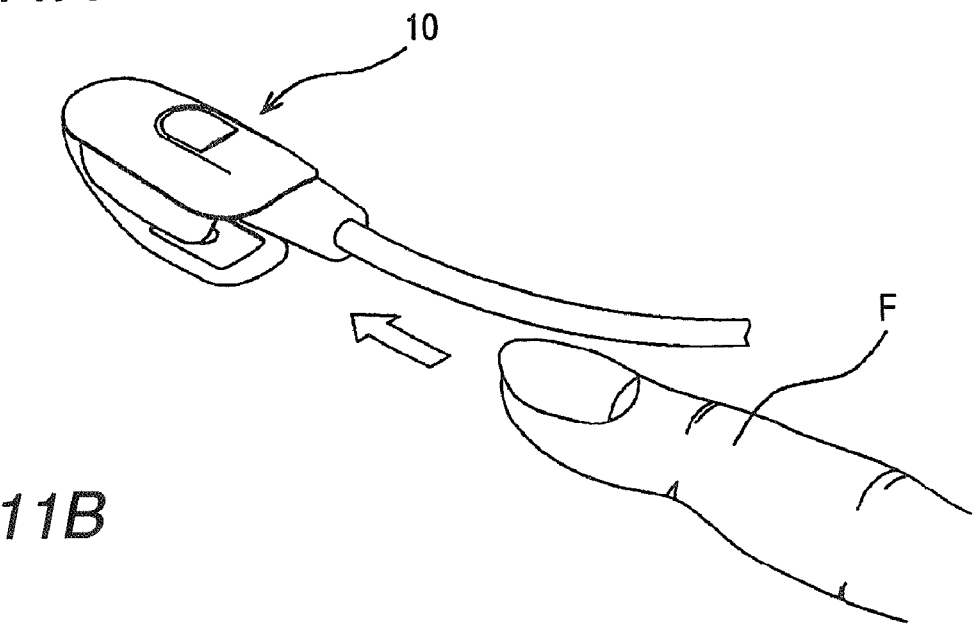
FIGS. 11A to 11C are views showing how to fix the probe on the finger of the subject.
Figure 11B:
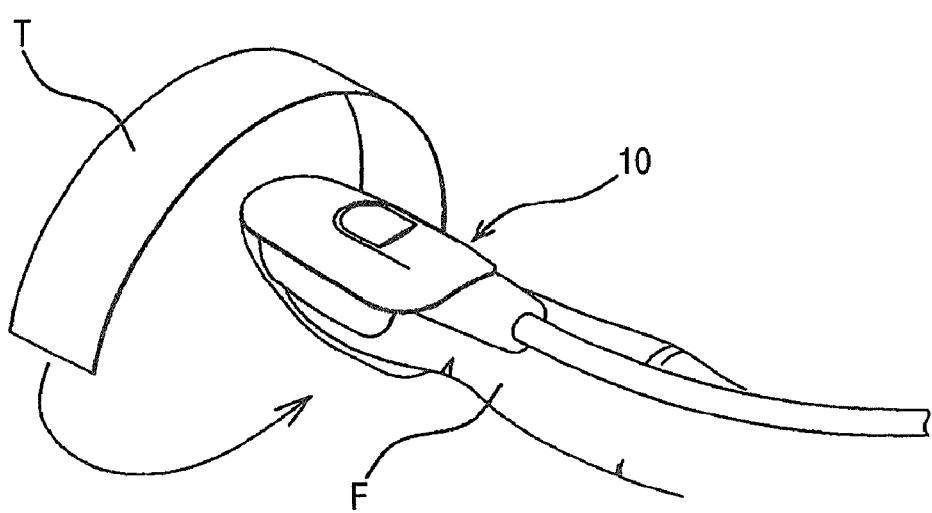
Figure 11C:
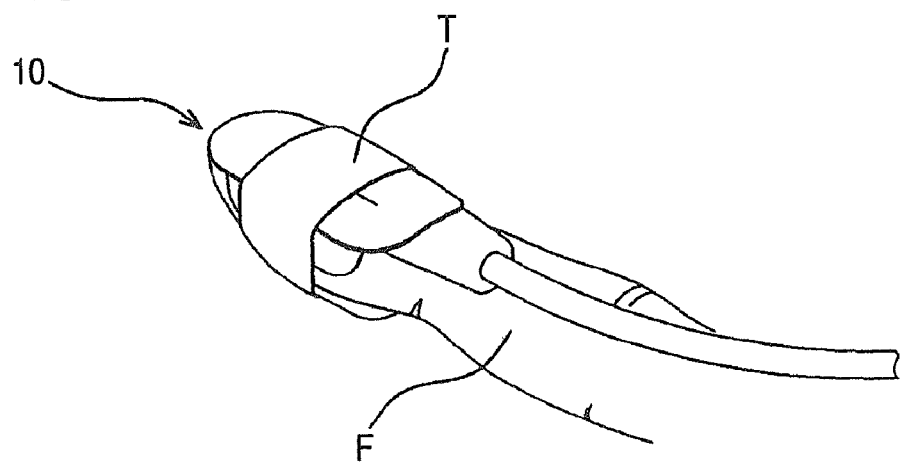

Next, operations for attaching the probe 10 to the tip end section F will be described. First, as shown in FIG. 11A, the probe 10 is attached to the tip end section F of the subject. In this case, the probe 10 can be tentatively, appropriately fixed to a predetermined measurement site by required flexural elasticity set between the first housing 12 and the second housing 14. Next, as shown in FIG. 11B, an adhesive tape T is wound around the probe 10 that is tentatively fixed to the predetermined measurement site. Accordingly, since the probe 10 is tentatively, appropriately fixed to the predetermined measurement site, the subject can readily perform the operation for winding such an adhesive tape T without fail. As shown in FIG. 11C, the probe 10 can be readily fixed and attached to the tip end section F by the adhesive tape T. When oxygen saturation of arterial blood is simply measured, the probe 10 may not be fixed with the adhesive tape T. Even in this case, the probe 10 of the present invention can be readily, appropriately used.

In the above embodiment, the light emitting element 20 is attached to the first housing 12 and the light receiving element 30 is attached to the second housing 14. However, the light emitting element 20 may be attached to the second housing 14 and the light receiving element 30 may be attached to the first housing 12.

In the above embodiment, the lead wire 24 is used to electrically connect the pulse oximeter with each of the light emitting element 20 and the light receiving element 30. However, the lead wire 24 may be replaced with a communicator which is electrically connected with each of the light emitting element 20 and the light receiving element 30, and is operable to communicate signals with the pulse oximeter in a wireless manner.

In the above embodiment, the probe is attached to a finger of a hand of a subject. However, the probe may be configured to be attached to a toe of a foot of a subject.

Although the present invention has been shown and described with reference to specific embodiments, various changes and modifications will be apparent to those skilled in the art from the teachings herein. Such changes and modifications as are obvious are deemed to come within the spirit, scope and contemplation of the invention as defined in the appended claims.

What is claimed is:

1. A probe adapted to be used with a pulse oximeter, comprising:
    a flexible first housing, adapted to be brought into contact with at least a nail of a finger or a toe of a subject;
    a flexible second housing, adapted to be brought into contact with at least a top of the finger or the toe;
    a flexible connecting part, connecting the first housing and the second housing, and adapted to cover a tip end of the nail;
    a light emitting element, provided on one of the first housing and the second housing; and
    a light receiving element, provided on the other one of the first housing and the second housing, wherein
    the first housing, the second housing and the connecting part are monolithically formed with flexible material comprised of resin so that the first housing and the second housing are adapted to be elastically brought into contact with a tip end portion of the finger or the toe, the elasticity of the connecting part causing the first and second housings to exert a pressure on the finger or the toe, the pressure being within a range suitable for pulse oximetry, the second housing is formed with an inclined surface adapted to be brought into contact with a pulp of the finger or the toe, and the first housing, the second housing and the connecting part are connected so as to define openings at opposite sides thereof.

2. The probe as set forth in claim 1, further comprising:
a cushion member, provided on the first housing and adapted to be brought into contact with the finger or the toe, the cushion member formed with an opening which allows light emitted from the light emitting element to pass therethrough.

3. The probe as set forth in claim 2, wherein a part of the opening is adapted to be opposed to a nail root of the finger or the toe.

4. The probe as set forth in claim 2, wherein the cushioning member includes a first part having a first softness, and a second part adapted to be opposed to a nail root of the finger or the toe and having a second softness softer than the first softness.

5. The probe as set forth in claim 1, further comprising:
a pair of light shielding covers, provided on the first housing and adapted to be opposed to side portions of the finger or the toe so as to entirely cover the nail of the finger or the toe.

6. The probe as set forth in claim 1, wherein a recess adapted to accommodate the tip end of the nail is formed on an inner face of the connecting part.

7. The probe as set forth in claim 1, wherein the pressure falls within a range from a first pressure at which a venous pulsation of peripheral blood vessels is reduced to a second pressure at which an arterial pulsation is not reduced.

8. The probe as set forth in claim 7, wherein the first pressure is 10 mmHg.

9. The probe as set forth in claim 7, wherein the second pressure is 35 mmHg.

10. The probe as set forth in claim 1, further comprising:
a lead wire, electrically connecting the pulse oximeter with each of the light emitting element and the light receiving element.

11. The probe as set forth in claim 1, further comprising:
a communicator, electrically connected with each of the light emitting element and the light receiving element, and operable to communicate signals with the pulse oximeter in a wireless manner.

* * * * *